United States Patent
Groenendaal et al.

(10) Patent No.: US 7,022,811 B2
(45) Date of Patent: Apr. 4, 2006

(54) 3,4-ALKYLENEDIOXYTHIOPHENE COMPOUNDS AND POLYMERS THEREOF

(75) Inventors: Bert Groenendaal, Sinaai (BE); John R. Reynolds, Gainesville, FL (US); Carleton L. Gaupp, Hilton, NY (US); Irina Schwendeman, Gibsonia, PA (US)

(73) Assignee: Agfa-Gevaert, Mortsel (BE)

( * ) Notice: Subject to any disclaimer, the term of this patent is extended or adjusted under 35 U.S.C. 154(b) by 38 days.

(21) Appl. No.: 10/680,546

(22) Filed: Oct. 7, 2003

(65) Prior Publication Data

US 2004/0072987 A1    Apr. 15, 2004

Related U.S. Application Data

(60) Provisional application No. 60/480,452, filed on Jun. 20, 2003, provisional application No. 60/416,565, filed on Oct. 7, 2002.

(51) Int. Cl.
 C08G 75/00   (2006.01)
 C08L 41/00   (2006.01)
(52) U.S. Cl. ............... 528/373; 528/377; 528/397; 528/401; 549/50; 524/800; 524/805; 524/817
(58) Field of Classification Search ........... 528/373, 528/377, 397, 401; 549/50; 524/800, 805, 524/817
See application file for complete search history.

(56) References Cited

U.S. PATENT DOCUMENTS 6,383,561 B1 * 5/2002 Moffat et al. ............ 427/180
6,439,711 B1 * 8/2002 Carlini et al. ............ 347/100

FOREIGN PATENT DOCUMENTS

EP    0 339 340 B1    11/1989
EP    0 440 957 B1    8/1991

OTHER PUBLICATIONS

Zhang et al.; *Chinese Journal of Polymer Science*, vol. 14(4), 330-337 (1996).
Zhang et al.; *Chinese Journal of Polymer Science*, vol. 15(1), 15-23 (1997).
Büchner et al.; *J. Electroanal. Chem.*, vol. 277, 355-358 (1990).

(Continued)

Primary Examiner—Duc Truong
(74) Attorney, Agent, or Firm—Leydig, Voit & Mayer

(57) ABSTRACT

A thiophene compound represented by formula (I):

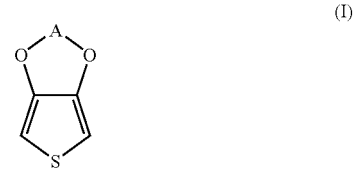

wherein A represents a $C_{1-5}$-alkylene bridge substituted with at least one fluorine atom and/or at least one alkyl group substituted with a fluorine-containing-group; polymers containing monomeric units of a thiophene compound represented by formula (I); a process for preparing polymers containing monomeric units of a thiophene compound represented by formula (I), optionally chemically or electrochemically; and solutions, dispersions, pastes and layers containing such polymers.

30 Claims, 4 Drawing Sheets

OTHER PUBLICATIONS

Callender et al.; *Optical Engineering*, vol. 32 (9), 2246-2253 (Sep. 1993).
Collard et al; *Polymer Preprints*, vol. 39 (1), 155-156 (Mar. 1998).
Collard et al.; *Polymeric Materials: Science and Engineering*, vol. 86, 38-39 (2002).
Hong et al; *Macromolecules*, vol. 32, 4232-4239 (1999).
Hong et al.; *Macromolecules*, vol. 33, 3502-3504 (2000).
Hong et al.; *Macromolecules*, vol. 33, 6916-6917 (2000).
Irvin et al.; *Polymers for Advanced Technologies*, vol. 9, 260-265 (1998).

* cited by examiner

3,4-ALKYLENEDIOXYTHIOPHENE COMPOUNDS AND POLYMERS THEREOF

CROSS-REFERENCE TO RELATED PATENT APPLICATIONS

This application claims the benefit of U.S. Provisional Application No. 60/416,565 filed Oct. 7, 2002, which is incorporated by reference. In addition, this application claims the benefit of U.S. Provisional Application No. 60/480,452 filed Jun. 20, 2003, which is also incorporated by reference.

FIELD OF THE INVENTION

The present invention relates to novel 3,4-alkylenedioxythiophene compounds, polymers containing monomeric units thereof and uses of such polymers.

BACKGROUND OF THE INVENTION

Numerous polythiophenes have been studied extensively due to their interesting electrical and/or optical properties. Polythiophenes become electrically conducting upon chemical or electrochemical oxidation or reduction.

EP-A 339 340 discloses a polythiophene containing structural units of the formula:

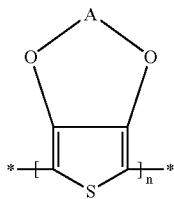

in which A denotes an optionally substituted $C_{1-4}$-alkylene radical and its preparation by oxidative polymerization of the corresponding thiophene.

EP-A 440 957 discloses dispersions of polythiophenes, constructed from structural units of formula (I):

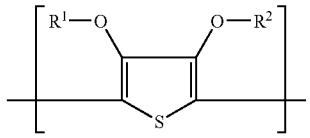

in which $R^1$ and $R^2$ independently of one another represent hydrogen or a $C_{1-4}$-alkyl group or together form an optionally substituted $C_{1-4}$-alkylene residue, in the presence of polyanions.

The preparation of poly(fluorinated 3-alkylthiophenes) was first reported by Buchner et al. in 1990 in Journal of Electroanalytical Chemistry and Interfacial Electrochemistry, volume 277, pages 355–358, who found that the strong inductive electron withdrawing effect of the perfluoroalkyl chain increased the oxidation potential of the thiophene ring compared to the non-fluorinated alkyl thiophene and the third-order optical nonlinearities in such polymers were reported by the same group in 1993 in Optical Engineering, volume 32, pages 2246–2254.

Zhang et al. in 1996 reported in the Chinese Journal of Organic Chemistry, volume 14, pages 330–337, the electrochemical polymerization of 3-fluoroalkoxy and 3-fluoroether thiophenes and in 1997 reported in the Chinese Journal of Organic Chemistry, volume 15, lines 15–23, that the introduction of a fluoroether functional group at the 3-position of the thiophene ring led to an increase in the oxidation potential of the monomer and to a decrease in the conductivity of the resulting polymers, even with the use of a methylene group as a spacer.

Over the period 1998 to 2002, Collard et al. have reported a number of studies concerning the synthesis and properties of semifluoroalkyl-substituted polythiophenes. In 1998 in Polymer Preprints, volume 39, pages 155–156, they reported the effect of perfluoroalkyl substituents on the surface properties and self-assembly of conjugated polymers; in 1999 in Macromolecules, volume 32, pages 4232–4239, they reported the synthesis of such polymers; in 2000 in Macromolecules, volume 33, pages 6916–6917, they reported controlling the macromolecular architecture of poly(3-alkylthiophene)s by alternating alkyl and fluoroalkyl substituents and in Macromolecules, volume 33, pages 3502–3504, they reported liquid crystalline regioregular semifluoroalkyl-substituted polythiophenes; and in 2002 in Polymeric Materials Science and Engineering, volume 86, pages 38–39, they reported that regioregular poly[3-alkylthiophene-alt-3-(semifluoroalkyl)-thiophene]s form highly-ordered solid-state lamellar structures with an interlayer spacing corresponding to a bilayer assembly. Furthermore, in 1998 Irvin and Reynolds in Polymers for Advanced Technologies, volume 9, pages 260–265, reported the synthesis, characterization and electrochemical polymerization of 1,4-bis[2-(3,4-ethylenedioxy)-thienyl]-2,5-difluorobenzene and 1,4-bis(2-thienyl)-2,5-difluorobenzene and the resultant polymers were found to be electroactive redox switchable films, with the more electron-rich ethylenedioxythiophene-derivative switching at lower potentials, and as thin films to exhibit electrochromic behaviour. However, no 3,4-alkylenedioxythiophenes [XDOT's] or polymers derived therefrom with direct substitution with fluorine atoms or alkyl groups substituted with a perfluoro-group have, to our knowledge, been reported in the literature.

There is a general requirement for new conductive polymers with unique combinations of optical and electrical properties.

ASPECTS OF THE INVENTION

It is therefore an aspect of the present invention to provide new 3,4-alkylenedioxythiophenes.

It is therefore another aspect of the present invention to provide polymers of the new 3,4-alkylenedioxythiophenes which exhibit improved optical properties.

Further aspects and advantages of the invention will become apparent from the description hereinafter.

SUMMARY OF THE INVENTION

Surprisingly it was found that poly[2,2,3,3,4,4,5,5,6,6,7,7,8,8,8-pentadecafluoro-octanoic acid 2,3-dihydro-thieno[3,4-b][1,4]dioxin-2-ylmethylester] (PEDOT-F) exhibited a relatively low oxidation potential, a fast switching time, a high visible contrast and had the ability to switch between a dark blue neutral state to a transmissive grey-blue state at easily accessible redox switching potentials with changes in transmittance as well as luminance of up to 63% combined with very high contact angles upon wetting and high electroconductivity.

Dual polymer electrochromic devices based on PEDOT-F and PBEDOT-NMeCz {poly[3,6-bis(2-ethylenedioxythienyl)-N-methyl-carbazole]} complementary polymers possessed the ability to operate at low applied voltages (±1.2V) with both films being compatible in the same electrochemical environment. They exhibited an optical contrast of up to 60% at $\lambda_{max}$ as well as an overall luminance change of 60%. Identical values for the change in luminance and transmittance is surprising, as in most electrochromic devices the transmittance at $\lambda_{max}$ is much higher than the overall luminance value. This implies that the device exhibits a broadband absorption in the dark state, with emphasis in the area where the eye is most sensitive, thus introducing a new dimension in electrochromic device construction.

Aspects of the present invention are realized with a thiophene compound represented by formula (I):

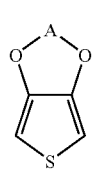

(I)

wherein A represents a $C_{1-5}$-alkylene bridge substituted with at least one fluorine atom and/or at least one alkyl group substituted with a fluorine-containing-group.

Aspects of the present invention are also realized by a polymer containing monomeric units of the above-mentioned thiophene compound.

Aspects of the present invention are also realized by a process for preparing the above-mentioned polymer.

Aspects of the present invention are also realized by a solution or dispersion containing the above-mentioned polymer in a liquid medium.

Aspects of the present invention are also realized by the use of the above-mentioned solution or dispersion for coating an object.

Aspects of the present invention are also realized by an ink or paste containing the above-mentioned polymer, the ink or paste being capable of being printed.

Aspects of the present invention are also realized by a first layer containing the above-mentioned polymer, the first layer exhibiting electroconductive properties.

Aspects of the present invention are also realized by a second layer containing the above-mentioned polymer, the second layer exhibiting antistatic properties.

Aspects of the present invention are also realized by a device containing the above-mentioned polymer, the device exhibiting electrochromic properties.

Further aspects of the present invention are disclosed in the dependent claims.

DETAILED DESCRIPTION OF THE INVENTION

FIGURE LEGENDS

DEFINITIONS

Figure 1:
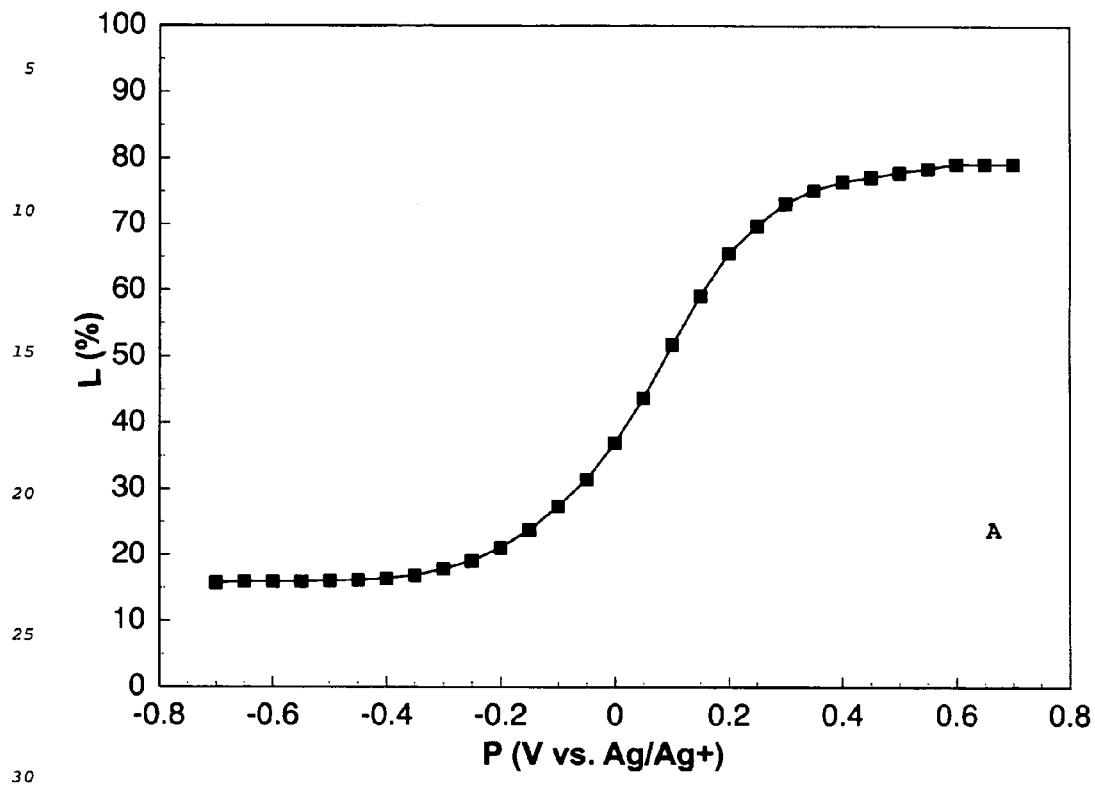
FIG. 1A represents a plot of relative luminance [L] as a function of the applied potential P in volts versus Ag/Ag$^+$ for PEDOT-F.
FIG. 1B represents a CIE 1931 x-y diagram recorded while the polymer was held at potentials ranging from −0.7 to +0.7 V vs. Ag/Ag$^+$.
Figure 1:
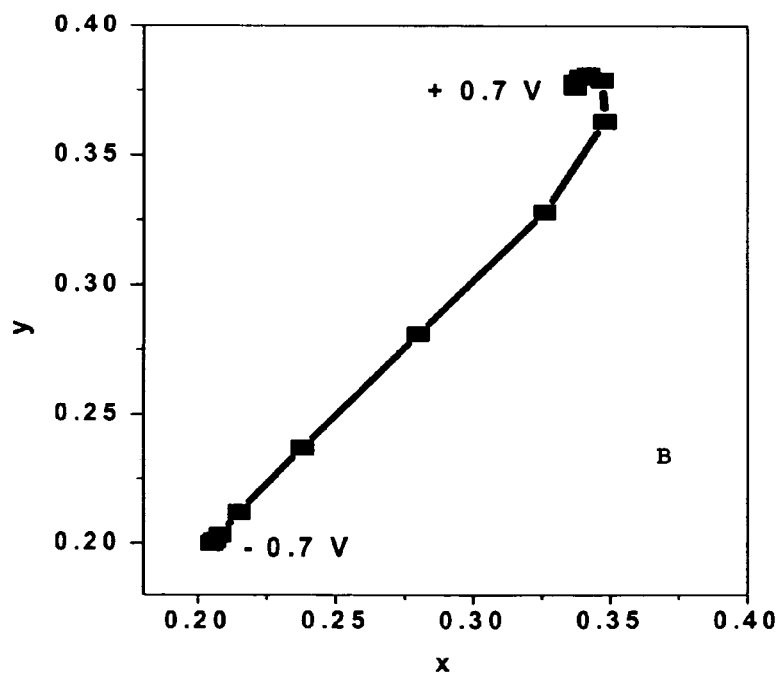

The term $C_{1-5}$-alkylene group represents methylenedioxy, 1,2-ethylenedioxy, 1,3-propylenedioxy, 1,4-butylenedioxy and 1,5-pentylenedioxy groups.

The term alkyl means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl etc.

The term polymer includes homopolymers, copolymers, terpolymers, graft polymers and block copolymers and both chain and condensation polymers.

The term perfluoro-group as used in disclosing the present invention refers to a group in which all the hydrogen atoms bonded to carbon atoms are replaced by fluorine atoms.

The term aqueous for the purposes of the present invention means containing at least 60% by volume of water, preferably at least 80% by volume of water, and optionally containing water-miscible organic solvents such as alcohols e.g. methanol, ethanol, 2-propanol, butanol, iso-amyl alcohol, octanol, cetyl alcohol etc.; glycols e.g. ethylene glycol; glycerine; N-methyl pyrrolidone; methoxypropanol; s and ketones e.g. 2-propanone and 2-butanone etc.

The term conductive layer as used in disclosing the present invention includes both electroconductive coatings and antistatic layers.

The term electroconductive means having a surface resistance below $10^6$ Ω/square.

The term antistatic means having a surface resistance in the range from $10^6$ to $10^{11}$ Ω/square meaning it cannot be used as an electrode.

The term "conductivity enhancement" refers to a process in which the conductivity is enhanced e.g. by contact with one or more high boiling point liquids such as di- or polyhydroxy- and/or carboxy groups or amide or lactam group containing organic compound optionally followed by heating at elevated temperature, preferably between 100 and 250° C., during preferably 1 to 90 seconds, results in conductivity increase. Alternatively in the case of aprotic compounds with a dielectric constant $\geq 15$, e.g. N-methyl-pyrrolidinone, temperatures below 100° C. can be used. Such conductivity enhancement is observed with polythiophenes and can take place during the preparation of the outermost layer or subsequently. Particularly preferred liquids for such treatment are N-methyl-pyrrolidinone and diethylene glycol such as disclosed in EP-A 686 662 and EP-A 1 003 179.

EDOT as used in the present disclosure represents 3,4-ethylenedioxythiophene.

EDOT-CH$_2$OH as used in the present disclosure represents 2-hydroxymethyl-2,3-dihydro-thieno[3,4-b][1,4]dioxine.

EDOT-F as used in the present disclosure represents 2,2,3,3,4,4,5,5,6,6,7,7,8,8,8-pentadecafluoro-octanoic acid 2,3-dihydro-thieno[3,4-b][1,4]dioxin-2-ylmethylester.

PEDOT-F as used in the present disclosure represents poly[2,2,3,3,4,4,5,5,6,6,7,7,8,8,8-pentadecafluoro-octanoic acid 2,3-dihydro-thieno[3,4-b][1,4]dioxin-2-ylmethylester].

PEDOT as used in the present disclosure represents poly(3,4-ethylenedioxythiophene).

ProDOT as used in the present disclosure represents 3,4-dihydro-2H-thieno[3,4-b][1,4]-dioxepine.

BEDOT-NMeCz as used in the present disclosure represents 3,6-bis(2-ethylenedioxythienyl)-N-methylcarbazole.

PBEDOT-NMeCz as used in the present disclosure represents poly[3,6-bis(2-ethylenedioxythienyl)-N-methylcarbazole].

PSS as used in the present disclosure represents poly(styrenesulfonic acid) or poly(styrenesulphonate).

PET as used in the present disclosure represents poly(ethylene terephthalate).

Thiophene Compound Represented by Formula (I)

Aspects of the present invention are realized with a thiophene compound represented by formula (I):

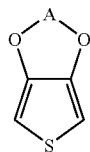

(I)

wherein A represents a C$_{1-5}$-alkylene bridge substituted with at least one fluorine atom and/or at least one alkyl group substituted with a fluorine-containing-group. Examples of fluorine-containing groups are perfluoro-alkylsulfonyl, perfluoro-arylsulfonyl, perfluoro-alkylsulfinyl, perfluoro-arylsulfinyl, perfluoroalkoxy, perfluoroaryloxy, perfluorothioalkoxy, perfluorothioaryloxy, perfluoroalkylcarbonato, perfluoroarylcarbonato, perfluoroalkylcarboxy, perfluoroarylcarboxy, perfluoroalkyloxo, perfluoroaryloxo, perfluoroalkylthioxo, perfluoroarylthioxo, perfluoroalkylamino, perfluoroarylamino, perfluoroalkyaminocarboxy, perfluoroarylaminocarboxy, perfluoroalkylaminothiocarboxy, perfluoroarylaminothiocarboxy, perfluoroalkyl, and perfluoroaryl.

According to a first embodiment of the thiophene compound, according to the present invention, A represents an ethylene group substituted with at least one fluorine atom and/or at least one alkyl group substituted with a perfluoro-group.

According to a second embodiment of the thiophene compound, according to the present invention, A represents an ethylene group substituted with a methylene-oxy-perfluoro-group.

According to a third embodiment of the thiophene compound, according to the present invention, the thiophene compound is a perfluoroalkylcarboxylic acid 2,3-dihydro-thieno[3,4-b][1,4]dioxin-2-ylmethylester.

According to a fourth embodiment of the thiophene compound, according to the present invention, the thiophene compound is 2,2,3,3,4,4,5,5,6,6,7,7,8,8,8-pentadecafluoro-octanoic acid 2,3-dihydro-thieno(3,4-b)(1,4)dioxin-2-ylmethylester.

According to a fifth embodiment of the thiophene compound, according to the present invention, the thiophene compound is 3,3-difluoro-3,4-dihydro-2H-thieno[3,4-b][1,4]-dioxepine.

Suitable thiophene compounds according to the present invention include:

| Thiophene compound nr. | Structural formula | |
|---|---|---|
| M1 | ![F,F,F,F substituted dihydro-thieno-dioxine] | 2,2,3,3-tetrafluoro-2,3-dihydro-thieno[3,4-b] [1,4]dioxine |
| M2 | ![F,F,F,F,F,F substituted dihydro-thieno-dioxepine] | 2,2,3,3,4,4-hexafluoro-3,4-dihydro-2H-thieno [3,4-b] [1,4]dioxepine |

-continued
| Thiophene compound nr. | Structural formula | |
|---|---|---|
| M3 | 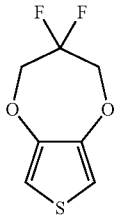 | 3,3-difluoro-3,4-dihydro-2H-thieno [3,4-b] [1,4]dioxepine |
| M4 | 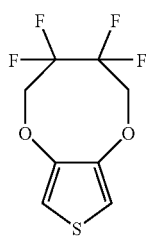 | 6,6,7,7-tetrafluoro-5,6,7,8-tetrahydro-4,9-dioxa-2-thia-cyclopentacyclooctene |
| M5 | 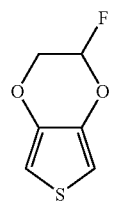 | 2-fluoro-2,3-dihydro-thieno[3,4-b] [1,4]dioxine |
| M6 | 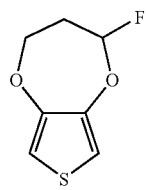 | 2-fluoro-3,4-dihydro-2H-thieno[3,4-b] [1,4]dioxepine |
| M7 | 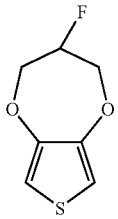 | 2-fluoro-3,4-dihydro-2H-thieno[3,4-b] [1,4]dioxepine |
| M8 | 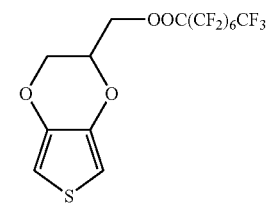 | 2,2,3,3,4,4,5,5,6,6,7,7,8,8-pentadecafluoro-octanoic acid 2,3-dihydro-thieno[3,4-b] [1,4]dioxin-2-ylmethyl ester |

-continued

| Thiophene compound nr. | Structural formula | |
|---|---|---|
| M9 | 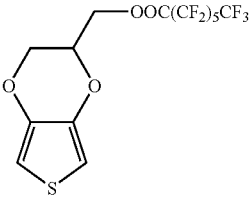 —OOC(CF$_2$)$_5$CF$_3$ | 2,2,3,3,4,4,5,5,6,6,7,7,7-tridecafluoro-heptanoic acid 2,3-dihydro-thieno[3,4-b] [1,4]dioxin-2-ylmethyl ester |
| M10 | 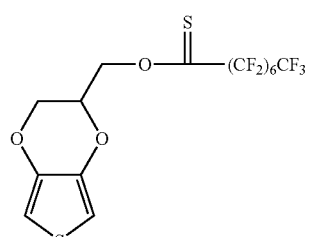 | 2,2,3,3,4,4,5,5,6,6,7,7,8,8,8-pentadecafluoro-octanethioic acid O-(2,3-dihydro-thieno[3,4-b] [1,4]dioxin-2-ylmethyl) ester |
| M11 | 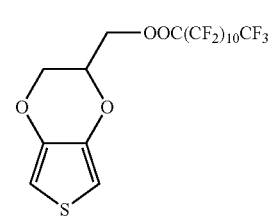 —OOC(CF$_2$)$_{10}$CF$_3$ | 2,2,3,3,4,4,5,5,6,6,7,7,8,8,9,9,10,10,11,11,12,12,12-tricosafluoro-dodecanoic acid 2,3-dihydro-thieno[3,4-b] [1,4]dioxin-2-ylmethyl ester |
| M12 | 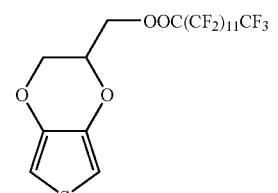 —OOC(CF$_2$)$_{11}$CF$_3$ | 2,2,3,3,4,4,5,5,6,6,7,7,8,8,9,9,10,10,11,11,12,12,13,13,13-pentacosafluoro-tridecanoic acid 2,3-dihydro-thieno [3,4-b] [1,4]dioxin-2-ylmethyl ester |
| M13 | 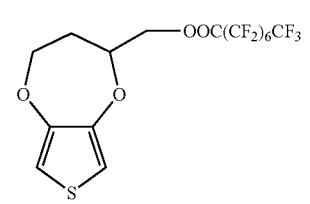 —OOC(CF$_2$)$_6$CF$_3$ | 2,2,3,3,4,4,5,5,6,6,7,7,8,8-pentadecafluoro-octanoic acid 3,4-dihydro-2H-thieno [3,4-b] [1,4]dioxepin-2-ylmethyl ester |
| M14 | 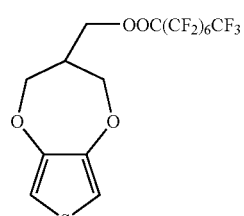 —OOC(CF$_2$)$_6$CF$_3$ | 2,2,3,3,4,4,5,5,6,6,7,7,8,8-pentadecafluoro-octanoic acid 3,4-dihydro-2H-thieno [3,4-b] [1,4]dioxepin-3-ylmethyl ester |
| M15 | CF$_3$(CF$_2$)$_6$COO— 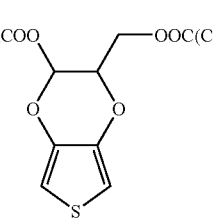 —OOC(CF$_2$)$_6$CF$_3$ | 2,2,3,3,4,4,5,5,6,6,7,7,8,8-pentadecafluoro-octanoic acid 3-(2,2,3,3,4,4,5,5,6,6,7,7,8,8,8-pentadecafluoro-octanoyloxymethyl)-2,3-dihydro-thieno [3,4-b] [1,4]dioxin-2-ylmethyl ester |

| Thiophene compound nr. | Structural formula | |
|---|---|---|
| M16 | [structure: EDOT-CH₂-O-S(=O)₂-(CF₂)₇CF₃] | 1,1,2,2,3,3,4,4,5,5,6,6,7,7,8,8,8-heptadecafluoro-octane-1-sulfonic acid 2,3-dihydro-thieno[3,4-b][1,4]dioxin-2-ylmethyl ester |
| M17 | [structure: EDOT-CH₂-O-S(=O)₂-(CF₂)₃CF₃] | 1,1,2,2,3,3,4,4,4-nonafluoro-butane-1-sulfonic acid 2,3-dihydro-thieno[3,4-b][1,4]dioxin-2-ylmethyl ester |
| M18 | [structure: EDOT-CH₂-O-C(=O)-O(CF₂)₃CF₃] | Carbonic acid 2,3-dihydro-thieno[3,4-b][1,4]dioxin-2-ylmethyl ester nonafluorobutyl ester |
| M19 | [structure: EDOT-CH₂-O-C(=O)-OC(CF₃)₃] | Carbonic acid 2,3-dihydro-thieno[3,4-b][1,4]dioxin-2-ylmethyl ester 2,2,2-trifluoro-1,1-bis-trifluoromethyl-ethyl ester |
| M20 | [structure: EDOT-CH₂-OOCO(CF₂)₆CF₃] | 2,2,3,3,4,4,5,5,6,6,7,7,8,8,8-pentadecafluoro-octaneperoxoic acid 2,3-dihydro-thieno[3,4-b][1,4]dioxin-2-ylmethyl ester |
| M21 | [structure: EDOT-CH₂-OC(CF₃)₃] | 2-(2,2,2-trifluoro-1,1-bis-trifluoromethyl-ethoxymethyl)-2,3-dihydro-thieno[3,4-b][1,4]dioxine |

-continued

| Thiophene compound nr. | Structural formula | |
|---|---|---|
| M22 | [structure with —O(CF₂)₆CF₃ substituent on 2,3-dihydro-thieno[3,4-b][1,4]dioxine] | 2-pentadecafluoroheptyl-oxymethyl-2,3-dihydro-thieno[3,4-b] [1,4]dioxine |
| M23 | [structure with —S(CF₂)₆CF₃ substituent on 2,3-dihydro-thieno[3,4-b][1,4]dioxine] | 2-pentadecafluoroheptyl-sulfanylmethyl-2,3-dihydro-thieno[3,4-b] [1,4]dioxine |
| M24 | [structure with —O—C(=O)—NH—(CF₂)₆CF₃ carbamate substituent on 2,3-dihydro-thieno[3,4-b][1,4]dioxine] | pentadecafluoroheptyl-carbamic acid 2,3-dihydro-thieno[3,4-b] [1,4]dioxin-2-ylmethyl ester |
| M25 | [structure with CFH—CFH bridge in propylenedioxythiophene] | |

3,4-Perfluoro-alkylenedioxythiophenes, such as M1 and M2, cannot be prepared using primary or secondary dihydroxy-perfluoro-alkanes, since such compounds appear not to be stable, the $CF_2OH$ or CFOH groups appearing to change into COF groups e.g. perfluorobutyrolactone is hydrolyzed by water to perfluorosuccinic acid. However, perfluorinated dihalides such as dibromo-perfluoro-alkanes, are stable and hence 3,4-perfluoro-alkylenedioxythiophenes, such as M1 to M3, can be prepared using a double Williamsson synthesis [see Pei et al. in 1994 in Polymer, volume 35, pages 1347–1351, for thiophene derivatives, and J. R. Reynolds et al. in 2001 in Journal of Organic Chemistry, volume 66, pages 6873–6882, and A. Merz et al. in 1995 in Synthesis, pages 795–800, for pyrrole derivatives], via the alkylation procedure reported by Halfpenny et al. in 2001 in Journal Chemistry Society, Perkins Transaction I, pages 2595–2603 who modified the alkylation procedure reported by Dallacker and Mues in 1975 in Chemische Berichte, volume 108, page 576 by using 1,2-dibromoethane instead of bromochloromethane, and via transetherification of 3,4-dimethoxythiophene (see Reynolds et al in 1999 in Advanced Materials, volume 11, pages 1379–1382). For example dibromodifluoromethane, 1,2-dichloro-tetrafluoro-ethane, 1,2-dibromo-tetrafluoro-ethane, a commercially available fire-extinguishing agent, 1,2-dibromohexafluoro-n-propane and 1,4-dichoro-octafluoro-n-butane, a good anaesthetic, can all be used.

Alternatively thiophene compounds with a perfluoro-$C_{1-5}$-alkylene bridge, such as M1 and M2, can be prepared from 3,4-alkylenedioxythiophene-2,5-dicarboxylic acid diesters by electrochemical perfluorination in anhydrous hydrogen fluoride, whereupon the $C_{1-5}$-alkylene bridge is perfluorinated and the thiophene ring is saturated by fluorine addition, followed by aromatisation of the product in the vapour phase by iron gauze at 500 to 600° C.

Thiophene compounds with a partially fluorinated $C_{1-5}$-alkylene bridge, such as M3 and M4, can be prepared from $HO—CH_2(CF_2)_nCH_2—OH$ compounds by condensation with 3,4-dialkoxythiophene-2,5-dicarboxylic acid diethyl ester or 3,4-dihydroxythiophene-2,5-dicarboxylic acid diethyl ester in a Mitsunobu reaction using the redox couple of a triaryl- or trialkylphosphine and an azodioxo-compound at a temperature between −40° C. and 160° C.

Alternatively a transetherification reaction can be used as disclosed in DE 3804522 and in HOUBEN-WEYL, volume VI/3, part 3, pages 171–173 (1971) using a thiophene derivative such as 3,4-dimethoxythiophene, such as described by D. M. Welsh et al. in 1999 in Polymer Preprints, volume 40(2), page 1206, regarding the synthesis of 3,4-(2',2'-dimethyl)-propylenedioxythiophene and 3,4-(2',2'-diethyl)propylenedioxythiophene, by L. J. Kloeppner et al. in 1999 in Polymer Preprints, volume 40(2), page 792 regarding the synthesis of 3,4-(2',2'-diethyl)propylenedioxythiophene, 3,4-(2',2'-dibutyl)propylene-dioxythiophene and 3,4-(2',2'-dioctyl)propylene-dioxythiophene, by Reynolds et al. in 1999 in Advanced Materials, volume 11, pages 1379–1382, and Roncali et al. in 2002 in organic Letters, volume 4, pages 607–609 regarding the synthesis of thieno [3,4-b]-1,4-oxathiane.

M5, M6 and M7 can be prepared from the corresponding hydroxy-compounds by converting the hydroxy-compound to the corresponding mesyl-compound by treatment with mesyl chloride and then treating the corresponding mesyl compound with potassium fluoride in, for example, diethylene glycol, analogously to the preparation of 2H-2,3-dihydro-3-fluor-1,5-benzodioxepin described in 1987 by P. Dionne et al. in Journal of the American Chemical Society, volume 109, pages 2616–2623.

Thiophene compounds with perfluoroalkylsulfonato, perfluoroarylsulfonato, perfluoroalkylsulfinyl, perfluoroarylsulfinyl, perfluoroalkylsulfinyl, perfluoroarylsulfinyl, perfluoroalkoxy, perfluoroalkylcarbonato, perfluoroarylcarbonato, perfluoroalkylcarboxy, perfluoroarylcarboxy, perfluoroarylaminocarboxy and perfluoroalkylaminocarboxy groups, such as M8 to M14, M16 to M22 and M24, can be prepared from a $C_{1-5}$-alkylene bridge substituted with a —$CH_2OH$ group, e.g. 2-hydroxymethyl-2,3-dihydro-thieno[3,4-b][1,4]dioxine [EDOT-$CH_2OH$], by conventional organic synthesis techniques e.g. ether is formation with perfluoro-alcohols, carbonato formation with phosgene and perfluor-alcohols, sulfonyl formation with a perfluoro-alkylsulphinyl chloride, carboxy formation with a perfluoroacyl chloride and aminocarboxy formation with a perfluoroalkyl isocyanate.

M25 can be prepared by adding a molecule of fluorine to the double bond of 2H-thienyl[3,4-b][1,4]dioxepine-6,8-dicarboxylic acid diethyl ester using lead tetrafluoride formed in situ from lead dioxide and hydrogen fluoride:

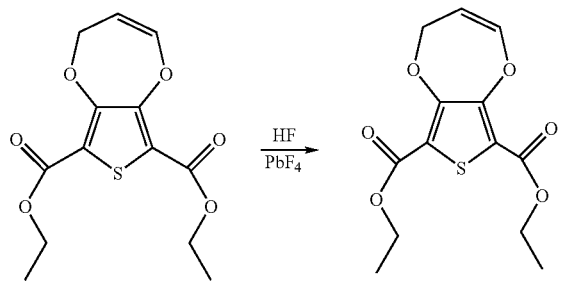

analogously to the procedure described by A. L. Henne et al. in 1945 in the Journal of the American Chemical Society, volume 67, page 1639, then hydrolyzing and finally decarboxylating the product following the procedures described by Kumar et al. in 1998 in Chemistry of Materials, volume 10, pages 896–902, to yield pure 3,4-[1,2-difluoropropylene]dioxythiophene, M25. 2H-thienyl[3,4-b][1,4]dioxepine-6,8-dicarboxylic acid diethyl ester with a melting point of 196–8° C. can itself be prepared in 54% yield by condensing the disodium salt of 3,4-dihydroxythiophene-2,5-dicarboxylic acid diethyl ester with epibromohydrin:

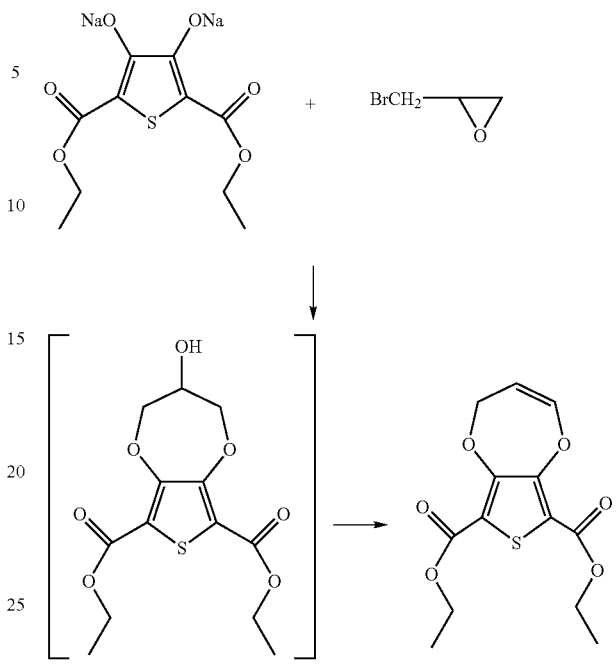

This diethyl ester can be hydrolyzed and decarboxylated following the procedures described by Kumar et al. in 1998 in Chemistry of Materials, volume 10, pages 896–902, to yield pure 2H-thienyl[3,4-b][1,4]dioxepine.

Perfluorinated dihalides can be prepared from perfluoroalkyldicarboxylic acids via the Hunsdieker reaction in which their silver salts are heated with the appropriate halogen with the loss of carbon dioxide e.g. the di-silver salt of perfluoroadipic acid upon heating with iodine at 100° C. yields the 1,4-di-iodide [Henne et al., J. Am. Chem Soc. 72, 3806 (1950) and Haszeldine, Nature 166, 192 (1950)].

HO—$CH_2(CF_2)_nCH_2$—OH compounds can be prepared by perfluorinating ClOC—$(CH_2)_n$—COCl compounds electrochemically in anhydrous hydrogen fluoride, hydrolyzing the FOC—$(CF_2)_n$—COF products and then reducing the resulting diacids to HO—$CH_2(CF_2)_nCH_2$—OH. Dimethyl fluoromalonate, Diethyl fluoromalonate, diethyl difluoromalonate, dimethyl tetrafluorosuccinate, dimethyl hexafluoroglutarate, dimethyl octafluoroadipate, perfluoroadipic acid, perfluorosebacic acid and perfluorosuberic acid are all commercially available from Interchim or BAYER. Perfluoromalonic acid can be prepared from chlorotrifluoroethylene [England et al., J. Am. Chem. Soc. 80, 6533 (1958)] or by fluorination of diethyl malonate with perchloryl fluoride [Inman et al., J. Am. Chem. Soc. 80, 6533 (1958)] and perfluorosuccinic acid by permanganate oxidation of perfluorocyclobutene.

Polymer Containing Monomeric Units of a
Thiophene Compound Represented by Formula (I)

Aspects of the present invention are realized with a polymer containing monomeric units of a thiophene compound represented by formula (I):

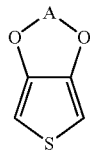

(I)

wherein A represents a $C_{1-5}$-alkylene bridge substituted with at least one fluorine atom and/or at least one alkyl group substituted with a fluorine-containing-group.

According to a first embodiment of a polymer, according to the present invention, the polymer contains monomeric units of a thiophene compound represented by formula (I) in which A represents a $C_{1-5}$-alkylene bridge substituted with at least one fluorine atom and/or at least one alkyl group substituted with a perfluoro-group.

According to a second embodiment of the polymer containing monomeric units of a thiophene compound represented by formula (I), according to the present invention, the polymer is selected from the group consisting of: poly(3,4-perfluoro-ethylenedioxythiophene), poly(3,4-perfluoro-propylenedioxy-thiophene), poly[3,3-difluoro-3,4-dihydro-2H-thieno[3,4-b][1,4]-dioxepine], poly[3,4-(2',2',3',3'-tetrafluoro-butylene)dioxythiophene] and poly[2,2,3,3,4,4,5,5,6,6,7,7,8,8,8-pentadecafluoro-octanoic acid 2,3-dihydro-thieno[3,4-b][1,4]dioxin-2-ylmethylester].

Polymerization Process

Aspects of the present invention are also realized with a process for preparing a polymer containing monomeric units of a thiophene compound represented by formula (I):

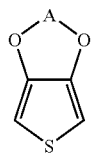

(I)

wherein A represents a $C_{1-5}$-alkylene bridge substituted with at least one fluorine atom and/or at least one alkyl group substituted with a perfluoro-group.

According to a first embodiment of the process, according to the present invention, the process is a chemical or an electrochemical process.

Chemical Polymerization

Chemical polymerization, according to the present invention, can be carried out oxidatively or reductively. The oxidation agents used for the oxidative polymerisation of pyrrole, such as described for example in Journal of the American Chemical Society, volume 85, pages 454–458 (1963) and J. Polymer Science Part A Polymer Chemistry, volume 26, pages 1287–1294 (1988), can be utilized for the oxidative polymerization of thiophenes.

According to a second embodiment of the polymerization process, according to the present invention, the process is a chemical process in which the inexpensive and easily accessible oxidation agents such as iron(III) salts such as $FeCl_3$, the iron(III) salts of organic acids, e.g. $Fe(OTs)_3$, $H_2O_2$, $K_2Cr_2O_7$, alkali and ammonium persulphates, alkali perborates and potassium permanganate are used therein to initiate the polymerization.

Theoretically the oxidative polymerization of thiophenes requires 2.25 equivalents of oxidation agent per mole thiophene of formula (I) [see e.g. J. Polymer Science Part A Polymer Chemistry, volume 26, pages 1287–1294 (1988)]. In practice an excess of 0.1 to 2 equivalents of oxidation agent is used per polymerizable unit. The use of persulphates and iron(III) salts has the great technical advantage that they do not act corrosively. Furthermore, in the presence of particular additives oxidative polymerization of the thiophene compounds according to formula (I) proceeds so slowly that the thiophenes and oxidation agent can be brought together as a solution or paste and applied to the substrate to be treated. After application of such solutions or pastes the oxidative polymerization can be accelerated by heating the coated substrate as disclosed in U.S. Pat. No. 6,001,281 and WO 00/14139 herein incorporated by reference.

Reductive polymerization can be performed using the Stille (organotin) or Suzuki (organoboron) routes described in 2002 by Appperloo et al. in Chem. Eur. Journal, volume 8, pages 2384–2396, and as disclosed in 2001 in Tetrahedron Letters, volume 42, pages 155–157 and in 1998 in Macromolecules, volume 31, pages 2047–2056 respectively or with nickel complexes as disclosed in 1999 in Bull. Chem. Soc. Japan, volume 72, page 621 and in 1998 in Advanced Materials, volume 10, pages 93–116.

Electrochemical Polymerization

Thiophene compounds according to formula (I) can be polymerized electrochemically. Electrochemical oxidative polymerization of thiophene compounds according to formula (I) carried out at temperatures from −78° C. to the boiling point of the solvent employed, temperatures between −20° C. and 60° C. is preferred. The reaction time, depending upon the particular thiophene, is generally between a few seconds and several hours. Electrochemical polymerization of thiophene compounds was described in 1994 by Dietrich et al. in Journal Electroanalytical Chemistry, volume 369, pages 87–92.

Inert liquids suitable for use during electrochemical oxidation of thiophene compounds according to formula (I) are: water, alcohols such as methanol and ethanol, ketones such as acetophenone, halogenated hydrocarbons such as methylene chloride, chloroform, tetrachloromethane and fluorohydrocarbons, esters such as ethyl acetate and butyl acetate, aromatic hydrocarbons such as benzene, toluene and xylene, aliphatic hydrocarbons such as pentane, hexane, heptane and cyclohexane, nitriles such as acetonitrile and benzonitrile, sulfoxides such as dimethylsulfoxide, sulfones such as dimethylsulfone, phenylmethylsulfone and sulfolan, liquid aliphatic amides such as methyl acetamide, dimethyl acetamide, dimethyl formamide, pyrrolidone, N-methylpyrrolidone, caprolactam, N-methyl-caprolactam, aliphatic and mixed aliphatic and aromatic ethers such as diethylether and anisole, liquid ureas such as tetramethylurea or N,N-dimethyl-imidazolidinone.

Electrolyte additives for use in the electrochemical polymerization of thiophene compounds according to formula (I) are preferably free acids or the usual conducting salts, which exhibit a certain solubility in the solvent used. Particularly suitable electrolytes are alkali, alkaline earth or optionally alkylated ammonium, phosphonium, sulfonium or oxonium cations in combination with perchlorate, tosylate, tetrafluoroborate or hexafluorophosphonate anions.

The electrolyte additives are used in such quantities, that a current of at least 0.1 mA flows during electrochemical oxidation.

Electrochemical polymerization can be carried out continuously or discontinuously. Known electrode materials are ITO-covered glass, precious metal or steel mesh, carbon-filled polymers, evaporated metal-coated insulator layers and carbon felt.

Current densities during electrochemical oxidation may vary within wide limits. According to an eighth embodiment of the present invention the current densities is 0.0001 to 100 mA/cm$^2$. According to a third embodiment of the process, according to the present invention, the current density is 0.01 to 40 mA/cm$^2$. At these current densities voltages of ca. 0.1 to 50 V are set up.

Thiophene compounds according to formula (I) may also be electrochemically copolymerized with other polymerizable heterocyclic compounds such as pyrrole.

Solution or Dispersion Containing a Polymer Containing Monomeric Units of a Thiophene Compound Represented by Formula (I)

According to a first embodiment of the solution or dispersion according to the present invention, the solution or dispersion further contains a polyanion.

According to a second embodiment of the solution or dispersion according to the present invention, the solution or dispersion further contains poly(styrenesulphonic acid).

According to a third embodiment of the solution or dispersion according to the present invention, the medium is an aqueous medium.

Polyanion

The polyanion compounds for use in the solution or dispersion according to the present invention are disclosed in EP-A 440 957 and include polymeric carboxylic acids, e.g. polyacrylic acids, polymethacrylic acids, or polymaleic acids and polysulphonic acids, e.g. poly(styrenesulphonic acid). These polycarboxylic acids and polysulphonic acids can also be copolymers of vinylcarboxylic acids and vinylsulphonic acids with other polymerizable monomers, e.g. acrylic acid esters, methacrylic acid esters and styrene.

Industrial Application

Chemically or electrochemically prepared polymers derived from thiophene compounds represented by formula (I) exhibit high electrical conductivity together with low absorption of visible light and high absorption to infrared radiation. Therefore layers thereof are highly electrically conducting, highly transparent to visible light and heat shielding. Such polythiophenes can be applied by a wide variety of techniques including printing techniques in which the polythiophene is applied, for example, as an ink or paste using standard techniques, the properties of the paste or ink being adapted to the particular printing technique by adding one of more of organic solvents, binders, surfactants and humectants, to a wide variety of rigid and flexible substrates, e.g. ceramics, glass and plastics, and are particularly suitable for flexible substrates such as plastic sheeting and the substrates can be substantially bent and deformed without the polythiophene layer losing its electrical conductivity. In view of the combination of high electroconductivity with high contact angles upon wetting, such polymers especially lend themselves to the production of electroconductive patterns.

Such polythiophenes can therefore be utilized, for example, in electrochromic devices, photovoltaic devices, batteries, capacitors and organic and inorganic electroluminescent devices, in electromagnetic shielding layers, in heat shielding layers, in antistatic coatings for a wide variety of products including photographic film, thermographic recording materials and photothermographic recording materials, in smart windows, in sensors for organic and bio-organic materials, in field effect transistors, in printing plates, in conductive resin adhesives and in free-standing electrically conductive films [see also chapter 10 of the Handbook of Oligo- and Polythiophenes, Edited by D. Fichou, Wiley-VCH, Weinheim (1999)].

The invention is illustrated hereinafter by way of comparative and invention examples. The percentages and ratios given in these examples are by weight unless otherwise indicated.

SYNTHESIS OF MONOMERS

Synthesis of (2,3-dihydro-thieno[3,4-b][1,4]dioxin-2-yl)-methanol (EDOT-CH$_2$OH) and 3,6-bis(2-ethylenedioxythienyl)-N-methyl-carbazole (BEDOT-NMeCz)

EDOT-CH$_2$OH and BEDOT-NMeCz were prepared following known procedures [Reddinger et al., J. Chem. Soc., Chem. Commun. 1777 (1996)].

Synthesis of 2,2,3,3,4,4,5,5,6,6,7,7,8,8,8-pentadecafluoro-octanoic acid 2,3-dihydro thieno[3,4-b][1,4]dioxin-2-ylmethylester (EDOT-F) (M8)

To a dry round bottom flask equipped with a Teflon stir bar and an argon inlet was added methylene chloride (20 mL), EDOT-MeOH (0.5 g, 2.9 mmol), and triethylamine (0.31 g, 3.1 mmol). To the stirring solution was added a solution of methylene chloride (20 mL) and the 2,2,3,3,4,4,5,5,6,6,7,7,8,8,8-pentadecafluoro-octanoic acid chloride (1.35 g, 3.13 mmol) dropwise via an addition funnel. The yellow solution was allowed to stir for 2 hours (30 minutes is sufficient) when it was poured into 100 mL of 1 M HCl. The organic layer was isolated and washed with concentrated NaHCO$_3$ (3×'s) followed by brine (3×'s). The organic layer was then dried over magnesium sulfate and concentrated under reduced pressure to yield an off-white/yellow solid. The solid was purified by flash column chromatography on silica gel (hexanes:methylene chloride, 7:3) to yield a white powder (0.82 g, 50%). Mp=64–65°. UV-vis (THF): $\lambda_{max}$=257 nm, $\epsilon$=5984.

$^1$H NMR (CDCl$_3$): δ 4.09 (dd, 1H, J=6.3, 11.8 Hz), 4.25 (dd, 1H, J=2.4, 11.8), 4.49 (m, 1H), 4.60 (m, 2H), 6.39 (s, 2H) ppm. $^{13}$C NMR (CDCl$_3$): δ 65.1, 65.7, 70.6, 100.7, 100.8, 140.5, 141.0, 158.2 ppm. $^{19}$F NMR (CDCl$_3$) δ −81.6 (CF$_3$), −118.8 (CF$_2$—CO), −122.0, −122.4, −123.0, −123.2, −126.6 (CF$_2$-CF$_3$) ppm. High resolution mass spectrometry calculated for C$_{15}$H$_7$F$_{17}$O$_4$S: 567.9826, found: 567.9825. Elemental analysis calculated for C$_{15}$H$_7$F15SO$_4$: C, 31.70%; H, 1.24%; F, 50.15%; S, 5.64%. Found: C, 31.69%; H, 1.28%; F, 47.91%; S, 6.52%.

After purification EDOT-F was handled under an inert atmosphere to prevent degradation.

Synthesis of 2,2-difluoro-1,3-propanediol 10 g (51.0 mmol) of difluoromalonic acid diethyl ester in 200 mL of tetrahydrofuran was added dropwise to a mixture of 19.0 g (505 mmol) of sodium borohydride in 100 mL of 50% aqueous ethanol with stirring at room temperature with water/ice cooling followed by stirring for 3 hours at room temperature. After adding 60 mL of a saturated solution carefully with cooling, the resulting mixture was filtered at pH 7–8 to separate the liquid phase from the solids. The solids were then washed with tert-butyl methyl ether and the washings added to the liquid phase. This organic solvents in this augmented liquid phase were then removed in a rotary evaporator and the aqueous phase remaining was extracted four times with tert-butyl methyl ether, dries with anhydrous magnesium sulphate and evaporated to dryness. The raw yield was 2.12 g. Fractionation distillation at 220° C. and a vacuum of 800 Pa (6 Torr) produced 1.57 g, corresponding to a yield of 27%, of 2,2-difluoro-1,3-propanediol as a largely solid product, as characterized by:

$^1$H NMR (CDCl$_3$): 1.148, 1.150, 1.171, 1.173, 1.195, 1.196, 1.905, 1.906, 1.985, 2.088, 2.494, 2.500, 2.506, 2.512, 2.538, 3.560, 3.605, 3.652, 3.694, 3.742, 3.788, 3.833, 4.015, 4.039, 4.628, 5.306 ppm.

Synthesis of 3,3-difluoro-3,4-dihydro-2H-thieno[3,4-b][1,4]-dioxepine-6,8-dicarboxylic acid diethyl ester 3,3-Difluoro-3,4-dihydro-2H-thieno[3,4-b][1,4]-dioxepine-6,8-dicarboxylic acid diethyl ester was synthesized by adding dropwise 3.4 mL (17.2 mmol) of azodicarboxylic acid diisopropyl ester (ADC) to a mixture of 1.77 g (6.67 mmol) of 3,4-dihydroxythiophen-2,5-dicarboxylic acid diethyl ester, 748 mg of 2,2-difluoro-1,3-propanediol and 4.3 mL of tributylphosphine in 12 mL of absolute tetrahydrofuran under argon at 20° C. with ice-cooling. After completion of the addition of ADC the resulting mixture was allowed to stand at room temperature for 4 days. The tetrahydrofuran was then distilled off and the residue heated for 12.5 hours at 100° C. after which it was dissolved in ethyl acetate. The ethyl acetate solution was washed three times with saturated sodium bicarbonate solution, then with deionized water, dried with anhydrous magnesium sulphate, concentrated and the residue chromatographically purified on a kieselgel 60 column with heptane/ethyl acetate as eluant. 335 mg (corresponding to a yield of 15%) of the desired product was obtained with a melting point of 121–122° C., as characterized by:

$^1$H NMR (CDCl$_3$): δ 1.370, 1.394, 1.418, 1.574, 4.338, 4.361, 4.364, 4.408, 4.512, 4.550, 4.588, 7.290; $^{13}$C NMR (CDCl$_3$): δ 14.194, 64.624, 71.545, 72.003, 72.452, 76.582, 77.000, 77.205, 77.422, 116.687, 116.917, 119.868, 123.148, 149.687 and 160.054 ppm.

Synthesis of 3,3-difluoro-3,4-dihydro-2H-thieno[3,4-b][1,4]-dioxepine-6,8-dicarboxylic acid 953 mg (3.67 mmol) of 3,3-Difluoro-3,4-dihydro-2H-thieno[3,4-b][1,4]-dioxepine-6,8-dicarboxylic acid diethyl ester in 75 mL of ethanol was mixed with 1.10 g (27.5 mmol) of sodium hydroxide granules and stirred for 2 hours under nitrogen at room temperature. After acidifying the resulting mixture with 2N hydrochloric acid, the ethanol was largely evaporated off using a rotary evaporator, the solids filtered off, the filtrate washed three times with water and then dried in air. 736 g of 3,3-difluoro-3,4-dihydro-2H-thieno[3,4-b][1,4]-dioxepine-6,8-dicarboxylic acid was obtained corresponding to a yield of 92% yield with a melting point of 288–293° C., as characterized by:

$^1$H NMR (CDCl$_3$): δ 1.169, 1.193, 1.216, 1.302, 1.325, 1.350, 1.959, 1.961, 2.035, 2.043, 2.050, 2.057, 2.065, 4.036, 4.059, 4.298, 4.321, 4.597, 4.603, 4.637, 4.643, 4.676 and 4.681 ppm (carried out on an unpurified product).

Synthesis of 3,3-difluoro-3,4-dihydro-2H-thieno[3,4-b][1,4]-dioxepine (M3)

300 mg (1.07 mmol) of 3,3-difluoro-3,4-dihydro-2H-thieno[3,4-b][1,4]-dioxepine-6,8-dicarboxylic acid was heated at 175° C. with 77 mg of copper chromite in 3.0 mL of quinoline for 1.5 hours. After cooling and mixing with 35 mL of tert-butyl methyl ether, the resulting mixture was washed three times with 2N hydrochloric acid, then three times with deionized water, dried with anhydrous magnesium sulphate and finally evaporated to dryness yielding 138 mg of raw product. The raw product was purified by column chromatography using Kieselgel 60 and cyclohexane as eluant. 82 mg of 3,3-difluoro-3,4-dihydro-2H-thieno[3,4-b][1,4]-dioxepine (M3) was obtained corresponding to a yield of 40% with a melting point of 66–67° C., as characterized by:

$^1$H NMR (DMSO): δ 4.258, 4.297, 4.335, 6.574 and 7.259 ppm; $^{13}$NMR (DMSO): δ 71.244, 71.694, 72.144, 76.582, 77.000, 77.422, 106.437, 116.993, 120.266, 123.538 and 147.420 ppm.

Synthesis of 2H-thieno[3,4-b][1,4]dioxepine-6,8-dicarboxylic acid diethyl ester 6.08 g (20 mmol) of the sodium salt of 3,4-dihydroxythiophene-2,5-dicarboxylic acid and 3.7 g (27 mmol) of epibromohydrin in 25 mL of ethanol were refluxed for 48 hours with stirring. After 2 hours a clear solution was obtained. After cooling the semi-solidified mass was mixed with acetic acid and 2N hydrochloric acid, shaken and the precipitated white crystals filtered off under reduced pressure. After washing with deionized water and drying 3.22 g (corresponding to a yield of 54%) of the desired product with a melting point of 196–198° C. Recrystallization from dioxan gave a colourless product with a melting point of 198–200° C. of the desired product with a melting point of 198–200° C., as characterized by:

$^1$H NMR (DMSO): δ 1.105, 1.182, 1.205, 1.229, 2.488, 2.494, 2.500, 2.506, 2.512, 2.524, 4.076, 4.089, 4.099, 4.112, 4.130, 4.136, 4.142, 4.150, 4.154, 4.178, 4.190, 4.201, 4.214, 4.477, 5.840, 5.889, 6.958, 7.007 ppm; $^{13}$NMR (DMSO): δ 14.344, 38.676, 38.949, 39.227, 39.777, 40.055, 40.328, 59.901, 60.419, 87.625, 120.528, 150.954, 160.670, 168.939 ppm.

The surface of this compound turned yellow on exposure to air over several days.

This diethyl ester can be hydrolyzed and decarboxylated following the procedures described by Kumar et al. in 1998 in Chemistry of Materials, volume 10, pages 896–902, to yield pure 2H-thieno[3,4-b][1,4]dioxepine:

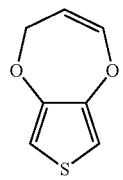

Electrochemical Polymerization EDOT-F (M8)

Oxidative electrochemical polymerization of EDOT-F (M8) was carried out in acetonitrile (ACN) with 0.1 M tetrabutylammonium perchlorate (TBAP) as electrolyte using an EG&G Princeton Applied Research model 273A potentiostat/galvanostat. A three-electrode cell was employed for the electropolymerization consisting of a Pt-disk working electrode (area=0.02 cm$^2$), a Pt flag counter-electrode, and a Ag/Ag$^+$ reference electrode. Electrodepositions were carried out via repeated oxidative on the Pt-disk from a 10 mM monomer solution in 0.1 M TBAP/CAN at a scan rate of 20 mV/s.

During the electropolymerization, no electrochemical response was evident at potentials negative of +1.0 V (vs. Ag/Ag$^+$, all further potentials will be reported vs. this reference). At +1.0 V, the current increased rapidly, peaking at +1.2 V. These values represent the onset of the polymerization and the peak monomer oxidation potential ($E_{p,m}$), respectively, and are shifted to slightly more positive potentials compared to EDOT.

Upon completion of the electrochemical polymerization, the polymer-coated electrode was washed with ACN and placed in a monomer-free electrolyte for electrochemical characterization.

Cyclic voltammograms of electrochemically polymerized PEDOT-F thin films were carried out using the same electrode setup only in monomer-free electrolyte (in 0.1 M TBAP/ACN) at scan rates of 50, 100, 150, 200 and 250 mV/s. The polymer displayed very well-defined and reversible redox processes with a half wave oxidation potential of −0.10 V, Corrware 2 from Scribner Associates being used for data acquisition.

Characterization of Electropolymerized PEDOT-F (M8)

Optical Properties

PEDOT-F was electrosynthesized potentiostatically at +1.2 V onto an ITO-coated glass substrate (area=1.0 cm$^2$) and the spectroelectro-chemical series of PEDOT-F examined using a Varian Cary 500 UV-vis-NIR spectrophotometer in a three electrode cell with an ITO-coated glass as the working electrode, a Pt wire as the counter and an Ag wire as a pseudo-reference. ITO-coated glass electrodes with surface resistivity less than 10 Ω were purchased from Delta Technologies, Ltd. Film thicknesses were measured utilizing a Dektak Sloan 3030 profilometer, the thickness given being the average of thickness taken in four areas of the films.

PEDOT-F was found to have an $E_g$ of 1.65 eV (taken by extrapolating the onset of the π–π* transition of the neutral polymer to the background absorbance) and a peak absorbance in the neutral form of 608 nm, similar to poly(3,4-ethylenedioxythiophene) [PEDOT]. At intermediate doping levels, the absorbance due to the π–π* transition diminished at the expense of a transition centered at about 1,000 nm (1.24 eV). At higher doping levels, this peak decreased in favour of a much broader absorption extending to wavelengths in the near-IR region of the spectrum.

Switching of PEDOT-F Between Neutral and Doped States

Data on the switching of PEDOT-F between the neutral and doped states was obtained by monitoring the transmission of monochromatic light at $\lambda_{max}$ during repeated redox stepping experiments. PEDOT-F was found to switch rapidly (0.6 s at 95%) between the colored neutral state and the highly transmissive doped state. The switching time for the polymer was taken at 95% of the full switch because beyond this point, it is difficult to perceive any further color change with the naked eye.

Composite Coloration Efficiency (CCE) and Doping Level

A key parameter for comparison between electrochromic materials is their composite coloration efficiency (CCE). A tandem chronoabsorptometry/chronocoulometry experiment was developed to measure coloration efficiency [CE] values at 95% of the optical density change.

EDOT-F potentiostatically electropolymerized at +1.2 V vs. a Ag/Ag$^+$ reference electrode to specific thicknesses (150 nm, as determined by profilometry in order to maximize the optical contrast) and areas (for charge density values) onto ITO-coated glass slides using a standard three-electrode system. Immediately following polymerization, PEDOT-F was rinsed and subsequently switched (in monomer-free electrolyte solution) between the doped and neutral states ten times in order to equilibrate the polymer film redox chemistry. Upon equilibration, films were transferred to a monomer-free electrolyte solution and probed with chronoabsorptometry (used to monitor the polymer absorbance at $\lambda_{max}$) and chronocoulometry as the potential was stepped from the fully reduced and absorbing state (−1.0 V vs. Ag/Ag$^+$ for 5 seconds), to the fully oxidized and transmissive state (+1.0 V for 5 seconds) and finally back to the fully reduced state (−1.0 V for 5 seconds). The change in optical density (ΔOD) as a function of injected charge was determined, and the CCE values were calculated.

The CCE is a function of the ratio of the change in optical density during a redox step and the charge injected as a function of the electrode area. Conducting polymers of the poly(3,4-alkylenedioxythiophene) family generally exhibit CCE values between 100 and 300 cm$^2$/C. CCE values of up to 586 cm$^2$/C, measured at 95% of the full transmittance change, were found for PEDOT-F. Surprisingly this value was a factor of two higher than that of PEDOT, making PEDOT-F highly suitable for electrochromic device type applications. Even though the transmittance change was similar to that for PEDOT, the charge required to p-dope was much smaller.

Relative Luminance Measurements

Luminance measurements were obtained with a Minolta CS-100 Chroma Meter and CIE recommended normal/normal (0/0) illuminating/viewing geometry for transmittance measurements. The samples were illuminated from behind by a D50 (5000 K) light source in a light booth specifically designed to exclude external light. A background measurement was taken using a blank ITO slide in an electrolyte solution held in a standard quartz cuvette. The Yxy values of the standard illuminant were measured and converted to the $X_n$, $Y_n$, $Z_n$ tristimulus values of the standard illuminant.

Electroconductivity of Electrochemically Polymerized Layers

Free-standing films were synthesized by constant current deposition from solutions containing 0.01 M monomer and 0.1 M TBAPF$_6$ in propylene carbonate. The electrochemical cell consisted of a glassy carbon working electrode and a stainless steel counter-electrode. The films were prepared by slow galvanostatic depostion at a constant current of 0.04 mA/cm$^2$ and the temperature was maintained at −5° C. Optimized conductivity values were typically obtained at low temperatures (0 to 5° C.), using TBAPF$_6$ as the electrolyte in a low vapor pressure solvent such as propylene carbonate acting as a plasticizer for the resulting film. Black, shiny, free standing films with thicknesses in the range of 15 μm were thereby electrosynthesized as measured with a micrometer. The films were peeled from the electrode, washed with acetonitrile and dried for 24 h.

Conductivities of up to 65 S/cm were measured with a four-point probe device called Signatone S-301-4.

Contact Angle and Contact Energy Measurements

Contact angle measurements were performed on thin (ca. 200 nm), $ClO_4^-$ doped films of PEDOT and PEDOT-F obtained by potentiostatic deposition on ITO/glass electrodes. After preparation, the films were rigorously washed with acetonitrile, then dried under vacuum for 24 hours. The measurements were performed ith a Contact Angle Meter model Cam-Plus from Tantec, Inc. and revealed striking differences in the hydrophobicity of the two materials. While the PEDOT surface was wettable, i.e. had a contact angle of less than 30°, PEDOT-F surface was highly hydrophobic, exhibiting a contact angle of 110°. This enhanced hydrophobicity is expected to have a beneficial effect on the environmental stability of neutral films. Moreover, it could lead to applications requiring the polymers to be stored in the neutral state without losing their electroactivity.

Contact energy measurements were carried out on PEDOT-F with a perchlorate counter-ion in oxidized state electropolymerized after 15 minutes degassing with nitrogen at 1.1V with 250 mC using an Ecochemie Autolab potentiostat type Pgstat 20 with GPES4.9 software by chronoamperimetrometry with a $2.5 \times 10^{-3}$ M solution of EDOT-F in acetonitrile with 0.1M tetrabutylammonium perchlorate as electrolyte on an acetone-cleaned 3×6 cm$^2$ ITO-glass electrode with a surface resistance of 60 Ω/square and with a 4×9 cm$^2$ platinum grid as counter-electrode. 0.1M Ag$^+$ in acetonitrile was used as the reference electrode. The surface energy measurements were carried out with a tilted plate configuration and 20–30 μL droplets were deposited on the PEDOT-F surface and static advancing and receding angles measured at an angle, in this case 85°, just before the droplet started to move. Deionized water and tricresylphosphate were used as the wetting liquids. The surface energy $\gamma_s$ was found to be 18.1 nM/m with the polar, $\gamma_s^p$, and dispersive, $\gamma_s^d$, components of the surface energy calculated from the average of the static and receding angles using the Owens-Wendt relationship [D. K. Owens and R. C. Wendt, J. Appl. Polymer Science 13, 1741 (1969)] being 0 mN/m and 18.1 mN/m respectively.

Colorimetry

Colorimetric techniques were used to study the optical properties of PEDOT-F. The luminance provides information about the s perceived transparency of a sample over the entire visible range of the spectrum. FIG. 1A shows the luminance dependence on the applied potential for PEDOT-F. The luminance increased upon oxidation from 16% to 79%, as the intensity of the π–π* transition diminishes. FIG. 1B represents the CIE 1931 x-y diagram for PEDOT-F showing that the polymer switches from a very dark blue neutral state at −0.5 V to a transmissive grey-sky blue oxidized state at 1 V.

Electrochromic Devices Containing PEDOT-F

PEDOT-F's surprising broad absorbance character, in combination with its increased hydrophobicity and expected enhanced solubility, makes it a viable candidate for electrochromic device applications.

An electrochromic device was constructed using transmissive windows based on PEDOT-F as cathodically coloring layer and PBEDOT-NMeCz as anodically coloring layer. The two polymer films were first electrochemically deposited on ITO/glass rinsed with freshly distilled acetonitrile.

A viscous gel electrolyte was then prepared by dissolving LiN(CF$_3$SO$_2$)$_2$ in a poly(methyl methacrylate) (PMMA) matrix plasticized with propylene carbonate [PC] to form a highly transparent and conductive gel. To allow easy mixing of the gel components, acetonitrile [ACN] was included as a high vapour pressure solvent. The composition of the casting solution by weight ratio of ACN:PC:PMMA:Li[N(CF$_3$SO$_3$)$_2$] was 70:20:7:3.

The selected cathodically and anodically coloring electrodes were then coated with the viscous gel electrolyte until the entire polymer surface was covered with a uniform and thin layer of electrolyte then applied to one another to form a viscous gel electrolyte sandwich and then allowed to dry for 24 hours. The gel electrolyte formed a seal around the edges, the devices becoming self-encapsulated. The device construction was carried out with one polymer oxidatively doped while the other was neutral.

Application of a voltage neutralized the doped polymer with concurrent oxidation of the complementary polymer, inducing color formation, or bleaching. The contrast of the device was optimized by matching the number of redox sites in each film to enable extremes of absorption and transmission to be attained by matching complementary polymer thicknesses.

Figure 2:
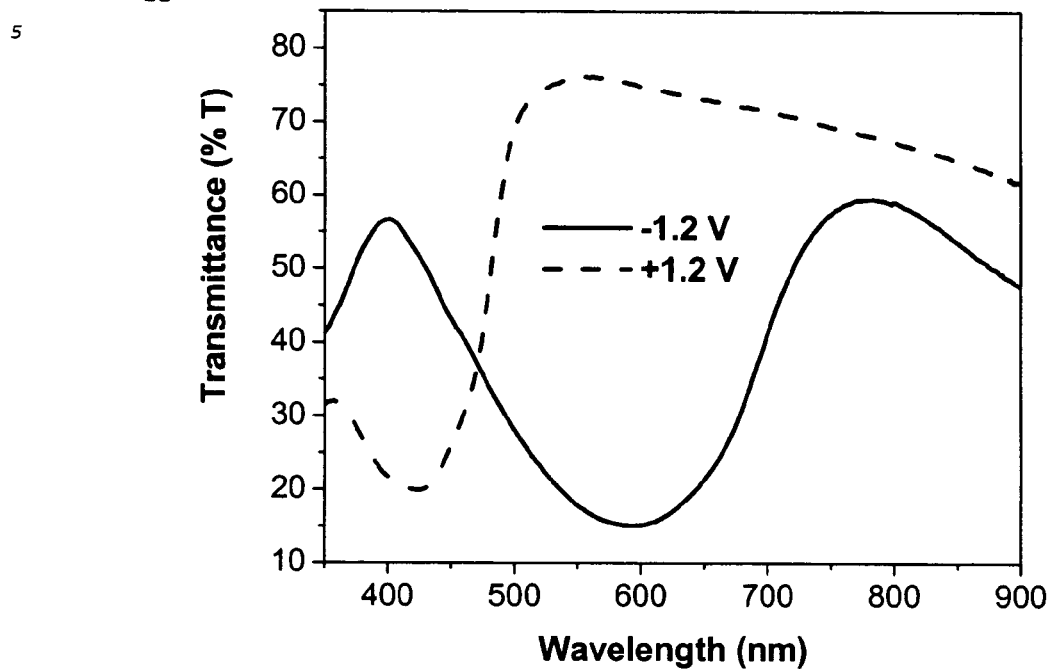
FIG. 2A represents the transmittance [T] in % for applied potentials of +1.2 (dashed line), the bleached state, and −1.2 V (continuous line), the colored state, as a function of wavelength [λ] in nm for the PBEDOT-NMeCz/PEDOT-F electrochromic device.
FIG. 2B represents the transmittance [T] in % as a function of time in seconds at a wavelength of 580 nm for the PBEDOT-NMeCz/PEDOT-F electrochromic device, showing the switching time.
Figure 2:
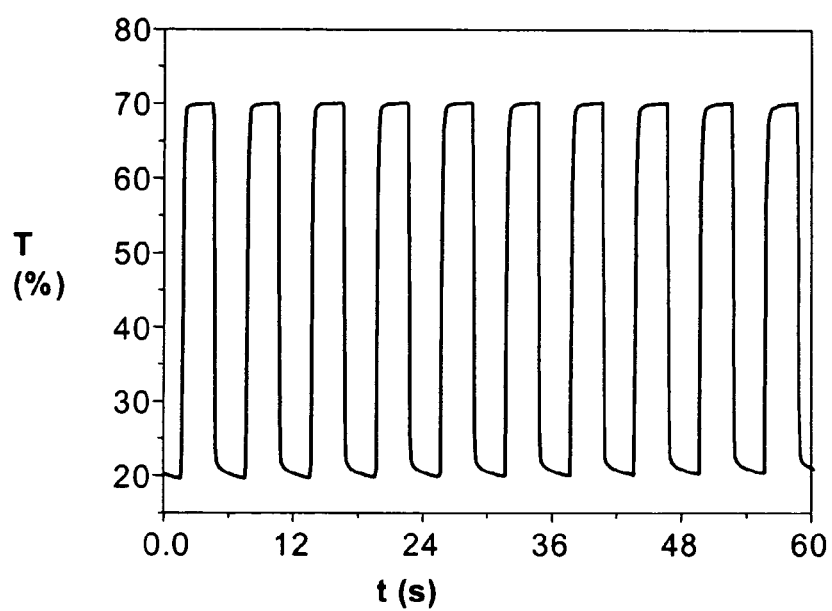

FIG. 2A represents the transmittance of the device assembled using 150 nm thick polymer films, as determined with a Dektrak Sloan 3030 profilometer. The device exhibited a contrast of 60% at 590 nm when a bias voltage of ±1.2 V was applied. Surprisingly the device exhibited a higher contrast than each polymer alone.

One of the most important characteristics of electrochromic devices is the response time needed to perform a switch from transmissive to opaque and vice versa. In order to analyze the switching characteristics of these windows, the change in transmittance at 580 nm was monitored during repeated redox switching experiments. The device attained 95% of the total transmission change in about 300 ms, as shown in FIG. 2B.

Figure 3:
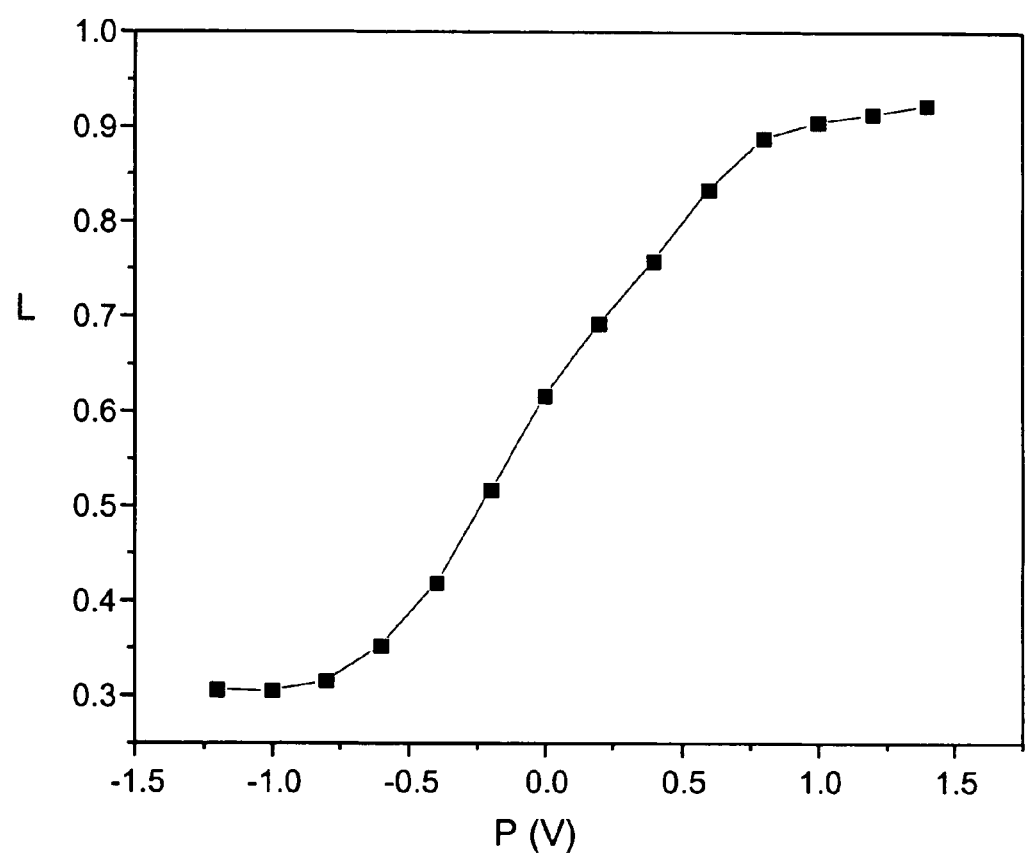
FIG. 3 represents the relative luminance [L] as function of the applied potential [P] in volts for the PBEDOT-NMeCz/PEDOT-F device.

Both luminance and x-y chromaticity diagrams provide valuable information for understanding changes in the device's color and/or brightness. The potential dependence on the relative luminance shown in FIG. 3 shows that, in the dark state, the window exhibited a relative luminance of 32%. The application of increasingly anodic potentials induced an increase in the relative luminance up to 92%, resulting in a highly transmissive film with a D%Y of 60%. The residual yellow color corresponds to the neutral state of the PBEDOT-NMeCz layer.

The combination of the properties of PEDOT-F and PBEDOT-NMeCz yielded a device that can reversibly switch between an opaque state and a highly transmissive state. A line that spans between a dark blue area of the color space to a highly transmissive yellow color is observed. This, together with substantial luminance and transmittance changes as well as fast switching times place devices based on PEDOT-F surprisingly at the forefront of organic electrochromic windows.

Electrochemical Polymerization of 3,3-difluoro-3,4-dihydro-2H-thieno[3,4-b][1,4]-dioxepine (M3)

The electrochemical polymerization of 3,3-difluoro-3,4-dihydro-2H-thieno[3,4-b][1,4]-dioxepine (M3) was carried out with a Princeton Applied Research Potentiostat/Galvanostat Model 273A and a 0.02 cm$^2$ Pt button working electrode, a Pt wire counterelectrode, and an Ag$^0$ wire pseudoreference electrode, which was then calibrated with a ferrocene solution in monomer-free elctrolyte solution. All potentials are reported versus ferrocene/ferricinium.

Figure 4:
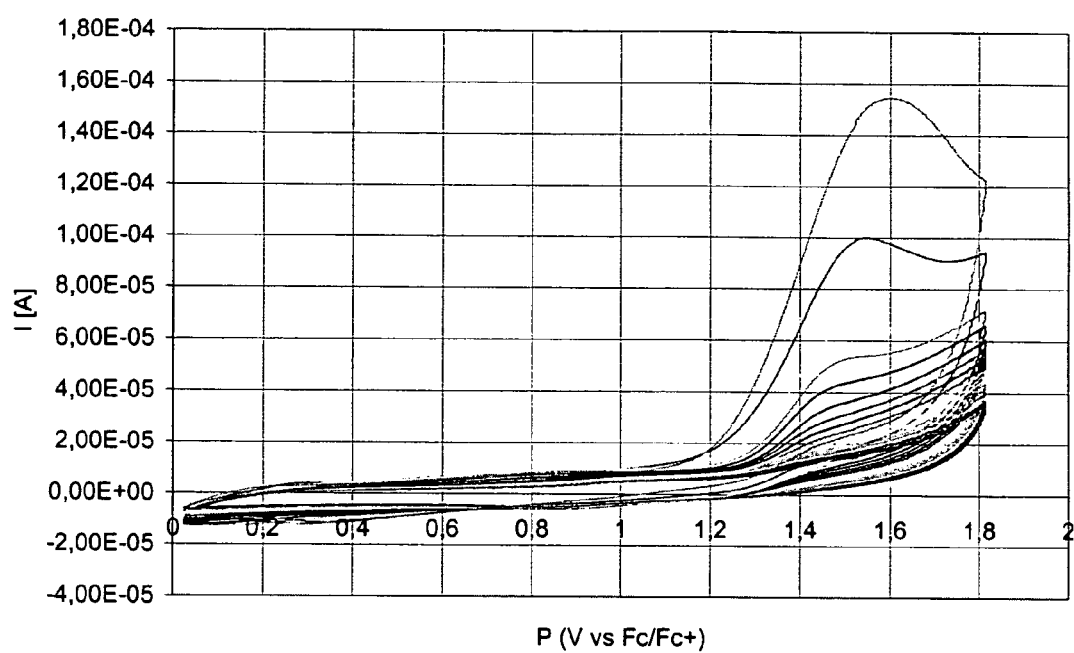
FIG. 4 represents successive CV-characteristics of 0.01M 3,3-difluoro-3,4-dihydro-2H-thieno[3,4-b][1,4]-dioxepine (M3) in a solution of 0.1M tetra-n-butyl-ammonium phosphorushexafluoride in dichloromethane in which the current in amps is plotted versus voltage versus ferrocene/ferrocenium.

FIG. 4 shows the CV characteristic of a solution 0.01M in M3 and 0.1M in tetra-n-butylammonium phosphorushexafluoride solution in dichloromethane. The first cycle shows that the peak oxidation potential of M3 is 1.6 V versus ferrocene-ferrocinium, which is surprisingly high compared with a value for ProDOT of 1.26–0.07=1.19 V versus ferrocene-ferrocinium (L. Groenendaal et al., Adv. Mater. 15, 855 (2003).

FIG. 4 also clearly shows that M3 electrochemically polymerizes as shown by the irreversible nature of the CV-characteristic.

Electrochemical Copolymerization of 3,3-difluoro-3,4-dihydro-2H-thieno[3,4-b][1,4]-dioxepine (M3) with EDOT and ProDOT Clear evidence of polymerization was found upon electrochemical polymerization of mixtures of 3,3-difluoro-3,4-dihydro-2H-thieno[3,4-b][1,4]-dioxepine (M3) with EDOT and ProDOT.

The present invention may include any feature or combination of features disclosed herein either implicitly or explicitly or any generalisation thereof irrespective of whether it relates to the presently claimed invention. In view of the foregoing description it will be evident to a person skilled in the art that various modifications may be made within the scope of the invention.

Having described in detail preferred embodiments of the current invention, it will now be apparent to those skilled in the art that numerous modifications can be made therein without departing from the scope of the invention as defined in the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A thiophene compound represented by formula (I):

wherein A represents a C$_{1-5}$-alkylene bridge substituted with at least one fluorine atom.

2. Thiophene compound according to claim 1, wherein A represents an ethylene group substituted with at least one fluorine atom.

3. Thiophene compound according to claim 1, wherein said thiophene is 3,3-difluoro-3,4-dihydro-2H-thieno[3,4-b][1,4]-dioxepine.

4. A polymer containing monomeric units of a thiophene compound represented by formula (I):

wherein A represents a $C_{1-5}$-alkylene bridge substituted with at least one fluorine atom.

5. Polymer according to claim 4, wherein said thiophene compound is 3,3-difluoro-3,4-dihydro-2H-thieno[3,4-b][1,4]-dioxepine.

6. A process for preparing a polymer containing monomeric units of a thiophene compound represented by formula (I):

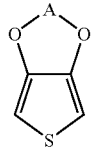

(I)

wherein A represents a $C_{1-5}$-alkylene bridge substituted with at least one fluorine atom.

7. Process according to claim 6, wherein said process is a chemical or an electrochemical process.

8. A solution or dispersion containing a polymer containing monomeric units of a thiophene compound represented by formula (I):

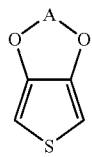

(I)

wherein A represents a $C_{1-5}$-alkylene bridge substituted with at least one fluorine atom in a liquid medium.

9. Solution or dispersion according to claim 8 further containing a polyanion.

10. Solution or dispersion according to claim 9, wherein said polyanion is poly(styrenesulphonic acid).

11. Solution or dispersion according to claim 8, wherein said liquid medium is an aqueous medium.

12. A process for using a solution or dispersion containing a polymer containing monomeric units of a thiophene compound represented by formula (I):

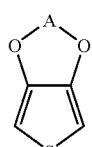

(I)

wherein A represents a $C_{1-5}$-alkylene bridge substituted with at least one fluorine atom in a liquid medium for coating an object.

13. An ink or paste containing a polymer containing monomeric units of a thiophene compound represented by formula (I):

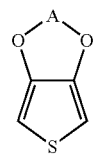

(I)

wherein A represents a $C_{1-5}$-alkylene bridge substituted with at least one fluorine atom said ink or paste being capable of being printed.

14. A first layer containing a polymer containing monomeric units of a thiophene compound represented by formula (I):

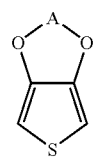

(I)

wherein A represents a $C_{1-5}$-alkylene bridge substituted with at least one fluorine atom, said first layer exhibiting electroconductive properties.

15. A second layer containing a polymer containing monomeric units of a thiophene compound represented by formula (I):

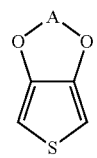

(I)

wherein A represents a $C_{1-5}$-alkylene bridge substituted with at least one fluorine atom, said second layer exhibiting antistatic properties.

16. A device containing a polymer containing monomeric units of a thiophene compound represented by formula (I):

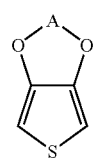

(I)

wherein A represents a $C_{1-5}$-alkylene bridge substituted with at least one fluorine atom, said device exhibiting electrochromic properties.

17. A thiophene compound represented by formula (I):

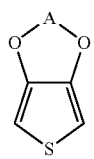

wherein A represents a $C_{1-5}$-alkylene bridge substituted with at least one fluorine atom and at least one alkyl group substituted with a fluorine-containing-group.

18. Thiophene compound according to claim 17, wherein A represents a $C_{1-5}$-alkylene bridge substituted with at least one fluorine atom and at least one alkyl group substituted with a perfluoro-group.

19. A polymer containing monomeric units of a thiophene compound represented by formula (I):

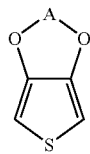

wherein A represents a $C_{1-5}$-alkylene bridge substituted with at least one fluorine atom and at least one alkyl group substituted with a fluorine-containing-group.

20. A process for preparing a polymer containing monomeric units of a thiophene compound represented by formula (I):

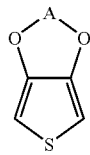

wherein A represents a $C_{1-5}$-alkylene bridge substituted with at least one fluorine atom and at least one alkyl group substituted with a fluorine-containing-group.

21. Process according to claim 20, wherein said process is a chemical or an electrochemical process.

22. A solution or dispersion containing a polymer containing monomeric units of a thiophene compound represented by formula (I):

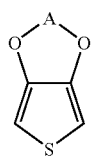

wherein A represents a $C_{1-5}$-alkylene bridge substituted with at least one fluorine atom and at least one alkyl group substituted with a fluorine-containing-group, in a liquid medium.

23. Solution or dispersion according to claim 22 further containing a polyanion.

24. Solution or dispersion according to claim 23, wherein said polyanion is poly(strenesulphonic acid).

25. Solution or dispersion according to claim 22, wherein said liquid medium is an aqueous medium.

26. A process for using a solution or dispersion containing a polymer containing monomeric units of a thiophene compound represented by formula (I):

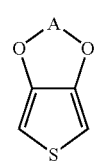

wherein A represents a $C_{1-5}$-alkylene bridge substituted with at least one fluorine atom and at least one alkyl group substituted with a fluorine-containing-group, in a liquid medium for coating an object.

27. An ink or paste containing a polymer containing monomeric units of a thiophene compound represented by formula (I):

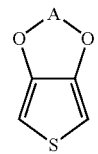

wherein A represents or a $C_{1-5}$-alkylene bridge substituted with at least one fluorine atom and at least one alkyl group substituted with a fluorine-containing-group, said ink or paste being capable of being printed.

28. A first layer containing a polymer containing monomeric units of a thiophene compound represented by formula (I):

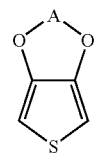

wherein A represents a $C_{1-5}$-alkylene bridge substituted with at least one fluorine atom and at least one alkyl group substituted with a fluorine-containing-group, said first layer exhibiting electroconductive properties.

29. A second layer containing a polymer containing monomeric units of a thiophene compound represented by formula (I):

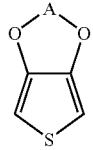

(I)

wherein A represents a $C_{1-5}$-alkylene bridge substituted with at least one fluorine atom and at least one alkyl group substituted with a fluorine-containing-group, said second layer exhibiting antistatic properties.

30. A device containing a polymer containing monomeric units of a thiophene compound represented by formula (I):

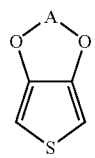

(I)

wherein A represents a $C_{1-5}$-alkylene bridge substituted with at least one fluorine atom and at least one alkyl group substituted with a fluorine-containing-group, said device exhibiting electrochromic properties.

* * * * *